(12) United States Patent
Link

(10) Patent No.: US 10,813,767 B2
(45) Date of Patent: Oct. 27, 2020

(54) REINFORCING IMPLANT FOR AN ELONGATED BONE, IN PARTICULAR FEMUR

(71) Applicant: WALDEMAR LINK GmbH & Co. KG, Hamburg (DE)

(72) Inventor: Helmut D. Link, Hamburg (DE)

(73) Assignee: WALDEMAR LINK GmbH & Co. KG, Hamburg (DE)

( * ) Notice: Subject to any disclaimer, the term of this patent is extended or adjusted under 35 U.S.C. 154(b) by 296 days.

(21) Appl. No.: 14/400,495

(22) PCT Filed: May 8, 2013

(86) PCT No.: PCT/EP2013/059589
§ 371 (c)(1),
(2) Date: Nov. 11, 2014

(87) PCT Pub. No.: WO2013/167655
PCT Pub. Date: Nov. 14, 2013

(65) Prior Publication Data
US 2015/0142124 A1  May 21, 2015

(30) Foreign Application Priority Data
May 11, 2012  (EP) .................................... 12167795

(51) Int. Cl.
*A61F 2/00* (2006.01)
*A61B 17/72* (2006.01)
(Continued)

(52) U.S. Cl.
CPC ............ *A61F 2/3859* (2013.01); *A61B 17/72* (2013.01); *A61F 2/28* (2013.01); *A61F 2/30721* (2013.01);
(Continued)

(58) Field of Classification Search
CPC .. A61F 2/3662; A61F 2/78; A61F 2002/0817; A61F 2002/0835;
(Continued)

(56) References Cited

U.S. PATENT DOCUMENTS

| | | | |
|---|---|---|---|
| 3,643,658 A * | 2/1972 | Steinemenan | A61B 17/58 |
| | | | 148/237 |
| 5,062,849 A | 11/1991 | Schelhas | |

(Continued)

FOREIGN PATENT DOCUMENTS

WO    WO-00/30569    6/2000

OTHER PUBLICATIONS

International Search Report and Written Opinion dated Jun. 11, 2013, directed to International Application No. PCT/EP2013/059589; 10 pages.

(Continued)

*Primary Examiner* — Ann Schillinger
(74) *Attorney, Agent, or Firm* — Joseph V. Saphia; Haug Partners LLP

(57) ABSTRACT

A reinforcing implant anchors shafts of two prostheses which are arranged opposite each other on an elongated bone, in particular a femur. The implant has a generally elongated shaft-like shape and a receiving sleeve at both ends for a respective anchoring shaft and a disconnectable coupling piece lying between the receiving sleeves for a rigid connection. In this manner, a force bridge is formed (Continued)

between the two anchoring shafts so that the bone is no longer subjected to the force transmission in particular in the sensitive intermediate region between the two anchoring shafts.

16 Claims, 4 Drawing Sheets

(51) Int. Cl.
*A61F 2/38* (2006.01)
*A61F 2/30* (2006.01)
*A61F 2/28* (2006.01)
*A61F 2/36* (2006.01)

(52) U.S. Cl.
CPC ............. *A61F 2/30734* (2013.01); *A61F 2/36* (2013.01); *A61F 2/38* (2013.01); *A61F 2002/2825* (2013.01); *A61F 2002/3092* (2013.01); *A61F 2002/30233* (2013.01); *A61F 2002/30357* (2013.01); *A61F 2002/30387* (2013.01); *A61F 2002/30433* (2013.01); *A61F 2002/30474* (2013.01); *A61F 2002/30507* (2013.01); *A61F 2002/30785* (2013.01)

(58) Field of Classification Search
CPC .... A61F 2002/30537; A61F 2002/3055; A61F 2002/30556; A61F 2002/30579; A61F 2002/30594; A61F 2002/30919; A61F 2002/4415; A61F 2220/0033
See application file for complete search history.

(56) References Cited

U.S. PATENT DOCUMENTS

| | | | | |
|---|---|---|---|---|
| 5,133,760 | A * | 7/1992 | Petersen | A61F 2/3676 623/20.34 |
| 5,334,184 | A * | 8/1994 | Bimman | A61F 2/28 606/63 |
| 5,358,524 | A * | 10/1994 | Richelsoph | A61F 2/4059 403/109.4 |
| 6,517,541 | B1 * | 2/2003 | Sesic | A61B 17/72 606/62 |
| 6,712,858 | B1 * | 3/2004 | Grundei | A61F 2/28 623/23.45 |
| 7,998,218 | B1 | 8/2011 | Brown | |
| 2004/0122440 | A1 * | 6/2004 | Daniels | A61F 2/36 606/102 |
| 2004/0172138 | A1 * | 9/2004 | May | A61B 17/164 623/20.36 |
| 2004/0193267 | A1 * | 9/2004 | Jones | A61F 2/28 623/16.11 |

OTHER PUBLICATIONS

International Preliminary Report on Patentability dated Nov. 20, 2014 and Written Opinion dated Jun. 11, 2013, directed to International Application No. PCT/EP2013/059589; 8 pages.

* cited by examiner

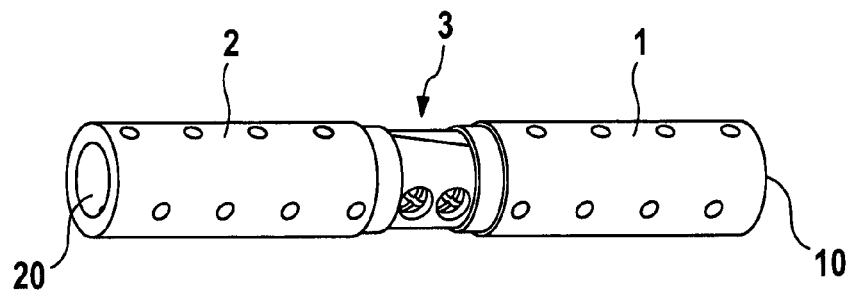
Fig. 1
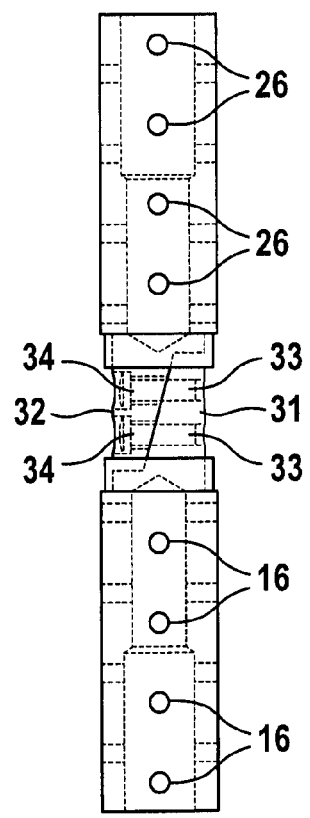 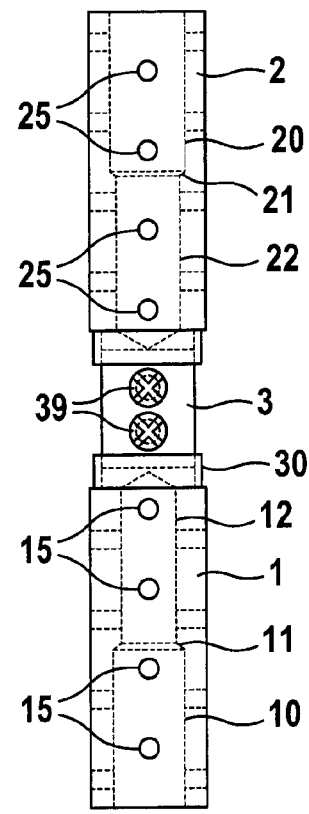
Fig. 2a    Fig. 2b

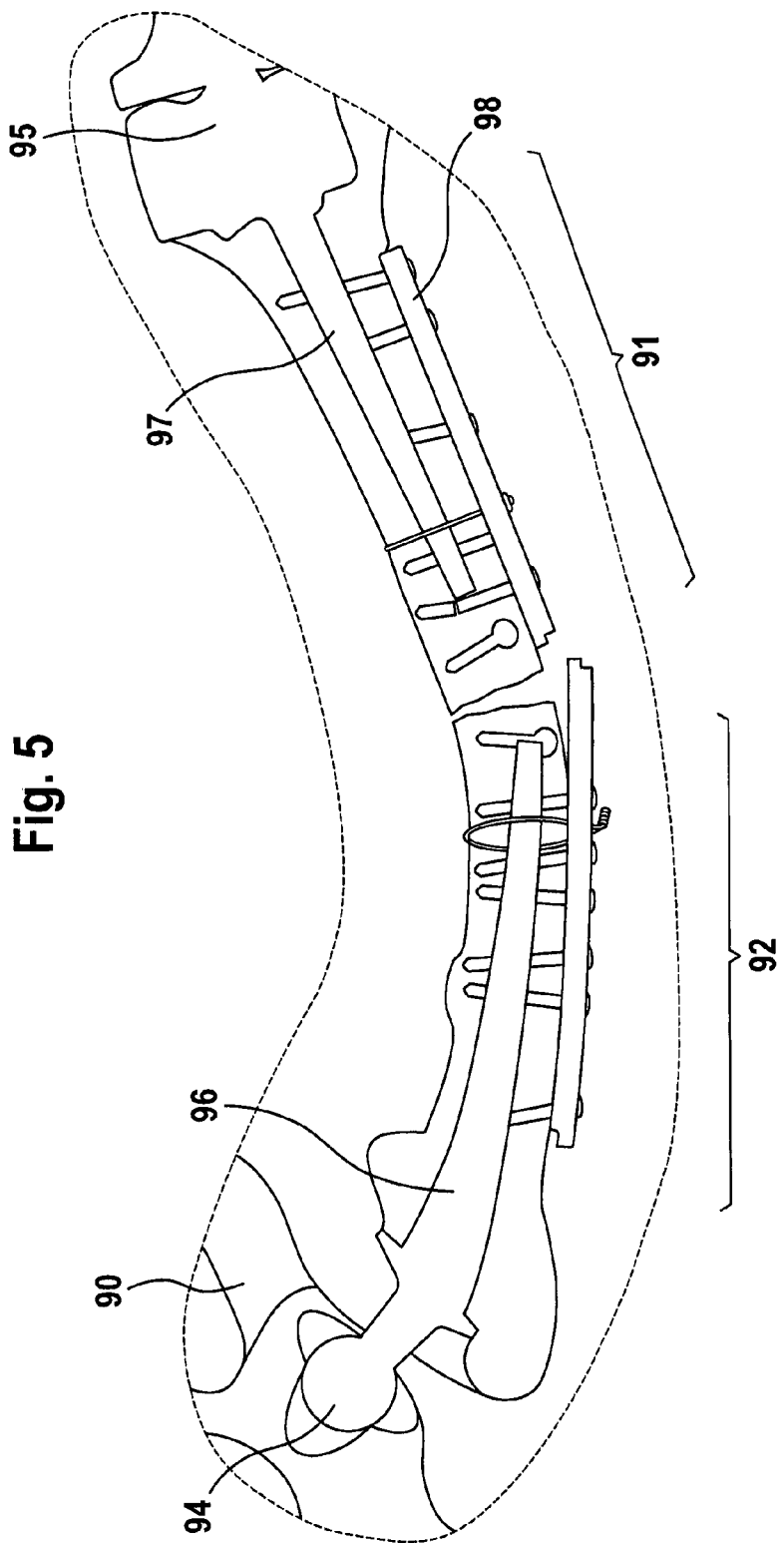

REINFORCING IMPLANT FOR AN ELONGATED BONE, IN PARTICULAR FEMUR

REFERENCE TO RELATED APPLICATIONS

This application is a national stage application under 35 USC 371 of International Application No. PCT/EP2013/059589, filed May 8, 2013, which claims priority to European Application No. 12 167 795.9, filed May 11, 2012, the entire contents of which are incorporated herein by reference.

FIELD OF THE INVENTION

The invention relates to a reinforcing implant for anchoring shafts of two prostheses which are arranged opposite each other on an elongate bone, in particular a femur.

BACKGROUND OF THE INVENTION

Prostheses, in particular joint prostheses, are often required in the area of the main extremities of the human body on account of wear or malformation. Here, the femur, or thigh bone, is of particular relevance in practice. Its upper end interacts with the hip joint, while its lower end interacts with the knee joint in humans. Hip operations involving implantation of an artificial hip joint are performed relatively often. The femoral part of a hip-joint prosthesis is then located at the upper end of the femur, said femoral part having a ball head which is secured by means of an anchoring shaft and which articulates with a mating piece arranged in the pelvis. The anchoring shaft carrying the ball head extends into the medullary canal of the femur and, depending on the design and size of the prosthesis, can reach to a considerable depth in the medullary canal. The same applies with respect to the knee joint, which is also very often the focus of an operation in which an artificial knee joint is implanted. As with the hip-joint prosthesis, the femoral part of the knee-joint prosthesis is also secured by an anchoring shaft, which is pushed into the medullary canal of the femur from below. In practice, it is not at all uncommon for a patient to have both joint prostheses implanted in a femur. This does not necessarily involve the prostheses being implanted at the same time; instead they are also often implanted at different times one after the other.

Although each of the two joint prostheses by itself has been found in practice to have good functionality and also lasting stability, a crucial factor in some cases is that the presence of two such joint prostheses in one femur may lead to a negative interaction. This is due in particular to the fact that the anchoring shafts inserted into the femur from both ends bring about a reinforcement of the femur in the respective end areas in which the anchoring shafts extend in the medullary canal of the femur. By contrast, the intermediate area in which neither of the two anchoring shafts extends is not reinforced. Although itself biologically sound, this intermediate area is thus relatively weakened by comparison with the end areas that are reinforced by the anchoring shaft, and it is therefore not uncommon for bone fractures to occur here as a result of the uneven distribution of force and, consequently, the particularly high degree of loading.

It is known that bone plates can be provided in order to reinforce the bone in the intermediate area. These bone plates have the advantage that their implantation is easy in practice and, moreover, they can also be readily implanted at a later stage. This latter point is particularly important when joint prostheses are implanted with an intervening period. In this case, the reinforcing bone plate only needs to be implanted when the second joint prosthesis (the knee prosthesis, for example, if a hip-joint prosthesis is already present) is implanted. A disadvantage of the bone plates is that they have to be relatively large in order to achieve sufficient mechanical stability, which correspondingly requires a considerably large surgical wound in the intermediate area of the femur. A further disadvantage that has been found in practice is that the stability of the reinforcement is often unsatisfactory. In particular, the screws used to fasten the bone plates in place are torn out, or the bone plate even breaks. It is difficult to strengthen the screws since the options available for arrangement of the screws are limited on account of the anchoring shafts already lying in the anchoring area of the bone screws. It has been found that reinforcement of the plates is likewise difficult, since there is only limited soft-tissue coverage in this area. The danger of the reinforcement by the bone plates failing is therefore not effectively counteracted, which poses additional risks for the patient who in any event has already undergone two difficult operations for implantation of joint prostheses.

SUMMARY OF THE INVENTION

An object of the invention is to make available a reinforcing implant which is of the type mentioned at the outset and which avoids these disadvantages.

This can be achieved by a reinforcing implant and implantation method as broadly disclosed herein. Advantageous developments are disclosed in the detailed embodiments described below.

In a reinforcing implant for anchoring shafts of two prostheses which are arranged opposite each other on an elongate bone, in particular a femur, provision is made according to the invention that the reinforcing implant has a generally elongate shaft-like shape and has a receiving sleeve at both ends for a respective anchoring shaft and, lying between the receiving sleeves, a disconnectable coupling piece for rigid connection of the two receiving sleeves.

An aspect of the invention is based on the concept whereby the two anchoring shafts are firmly gripped with the receiving sleeves and are connected to each other with a force fit by the coupling piece provided on the reinforcing implant. In this way, a force bridge is formed between the two anchoring shafts, such that the bone is no longer subject to the force transmission in particular in the sensitive intermediate area between the two anchoring shafts. This helps preserve the bone. It also provides a more even distribution of force in the bone, since the latter is now reinforced along the entire length of its femoral canal. Warping in relation to the stability of the bone is thereby effectively avoided. This has the effect that fractures no longer occur in the intermediate area.

The receiving sleeves are preferably designed as universal sockets for anchoring shafts with different dimensions. This allows different types and sizes of joint prostheses to be received via their anchoring shafts and securely anchored. This is particularly important since, specifically in the case of prostheses that are implanted at different times, it is not possible to rule out the possibility of the joint prosthesis at one end originating from a different manufacturer than the joint prosthesis at the other end, with the result that the anchoring shafts are of entirely different configuration. The universal socket in the sleeve ensures that secure and reliable fastening is achieved in this case too. To this end, the receiving sleeve is expediently designed such that a receiving bore arranged in it is stepped in terms of its width. This means that the outer area of the receiving bore has a greater width than an area of the receiving bore toward the inside, i.e. an area toward the coupling piece. A stepped receiving bore of this kind not only allows shafts of different width and different diameter to be safely received, it also permits a particularly secure mounting of anchoring shafts that have conical end areas.

In order to lock the anchoring shafts in the receiving sleeve and to avoid accidental migration out of the receiving sleeve, several fastening holes are preferably arranged in rows on the receiving sleeve. The fastening holes are designed to receive fastening screws. In this way, the anchoring shaft can be clamped firmly in the receiving sleeve. Sufficiently strong and stable fastening is thus achieved even under considerable loading and over long periods of time of up to several years. The fastening holes are preferably axially offset about the circumference. This also permits secure fastening of anchoring shafts that are not rotationally symmetrical in shape.

To ensure secure anchoring, the fastening screws are preferably provided with conical tips. Through high surface pressure on the outer jacket of the anchoring shaft, this ensures secure fastening free of wobble. It is particularly preferable if the tip is made of a hard metal which, by virtue of its hardness, is able to penetrate the outer jacket of the shaft. This provides even more secure fastening.

The fastening holes are advantageously provided with securing devices which prevent accidental loosening of the fastening screws. This achieves a high level of safety of the fastening, even over long periods of time amounting to years or decades. The securing devices can be in the form of plastic inserts.

The receiving sleeve is expediently dimensioned to be so long that its length is at least three times the width of the anchoring shaft. It has been found that a better and more stable connection in the femur can be achieved when there is such a relatively long support of the anchoring shaft. This is particularly important specifically in the case of the femur, since the length of the latter can result in considerable lever forces on the two joint prostheses involved, hip and knee.

By contrast, the coupling piece is expediently short. Here, short is understood as meaning that the length of the coupling piece is not greater than the width of the receiving sleeve. In this way, specifically in the highly loaded area of the coupling piece, a lower load is achieved by shortening the lever arms. The stability of the reinforcing implant according to the invention increases as a result.

The coupling piece is advantageously designed as a wedge action connector. The latter has the advantage of allowing the two components, i.e. the two receiving sleeves, to be fastened free of play, even when subjected to a high force.

The wedge action connector is preferably designed such that it comprises two flat wedges arranged in opposite directions. Arranged in opposite directions is understood as meaning that each of the two flat wedges is arranged on one of the two receiving sleeves and extends in the direction of the other one. Flat wedges are understood as wedges with on the substantially rectangular cross section, wherein the height of the rectangle continuously decreases toward the tip depending on the position on the wedge. This results in a particularly compact and load-bearing connection in the coupling piece.

Locking screws are advantageously provided for the wedge action connector. They allow the wedge action connector to be fixed free of play during the operation but nevertheless also allow the connection to be undone if re-implantation proves necessary. The locking screws are preferably implanted such that they are in line with at least one row of fastening holes on the receiving sleeve. This facilitates access to the screws during the operation.

The invention further relates to a method for implanting a reinforcing implant as described above, which method involves pushing the receiving sleeves onto the ends of the anchoring shafts, securing the receiving sleeves, creating a lateral access opening in the central area of the elongate bone, inserting the receiving sleeves with the anchoring shafts from the direction of the respective end of the bone, and connecting the coupling piece and securing the coupling piece via the access opening. For further explanation, reference is made to the above description.

BRIEF DESCRIPTION OF THE DRAWINGS

The invention is explained in more detail below with reference to the attached drawing which shows an advantageous illustrative embodiment. In the drawing:

FIG. 1 shows a perspective view of an illustrative embodiment of a reinforcing implant;

FIGS. 2a and 2b show a plan view and a side view, respectively, of the illustrative embodiment shown in FIG. 1;

FIG. 5 shows a fracture of the femur without reinforcing implant, as seen on an X-ray image.

DETAILED DESCRIPTION OF THE INVENTION

Figure 3:
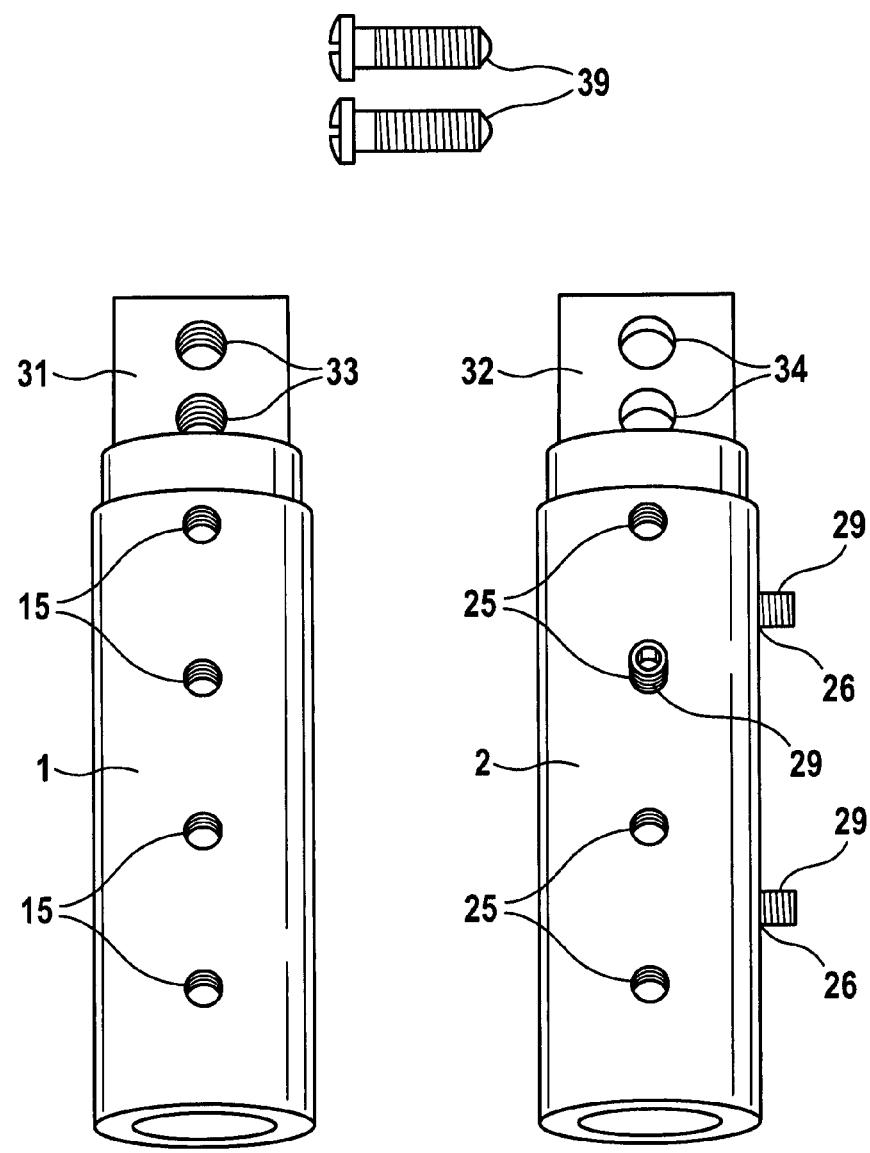
FIG. 3 shows a view of the individual parts of the reinforcing implant according to the first illustrative embodiment.

An illustrative embodiment of a reinforcing implant according to the invention is described below. It comprises as its main components a receiving sleeve 1, at each of its two ends and, between these, a coupling piece 3. The receiving sleeve 1 is arranged on the distal side, i.e. on the side directed toward the end of an extremity of the body, while the receiving sleeve 2 is arranged on the proximal side.

The structure of the two receiving sleeves 1, 2 is described below. This is done taking the example of the distal receiving sleeve 1. The proximal receiving sleeve 2 is of identical structure and insofar need not be dealt with separately. The distal receiving sleeve 1 is of substantially hollow cylindrical shape with a smooth outer jacket. It is preferably made of a biocompatible metal material, in particular cobalt chromium molybdenum (CoCrMo). Its external diameter is chosen such that it is not larger than the width of the bone on which the implantation procedure is performed. In the illustrative embodiment shown, the reinforcing implant is provided for implantation on a femur 9.

In its interior, the receiving sleeve 1 has a cavity 10 extending in the axial direction. This cavity 10 has a stepped configuration, with a shoulder 11 located about half way along it, which shoulder 11 is adjoined by an area with a narrowed diameter 12. The interior 10 opens out at an end face of the receiving sleeve 1. Rows of holes are formed in pairs respectively opposite each other in the jacket of the receiving sleeve 1. Four holes 15 are respectively arranged on a front and rear face (see FIG. 2b), while four holes 16 are likewise arranged axially offset on the two lateral faces (see FIG. 2a). The offset is chosen such that one of the holes in the row of holes 16 is arranged approximately centrally between the holes in the row of holes 15, and vice versa. This can be seen clearly from FIG. 1. The receiving holes are preferably provided with a thread for receiving a fastening screw 29 (see FIG. 3). The receiving holes 15, 16 are oriented such that they point to the central axis of the interior 10. As will be explained in more detail below, they serve to secure an anchoring shaft that is pushed into the receiving space.

A wedge element 31 of the coupling piece 3 is arranged at the end of the proximal receiving sleeve 1 opposite the end face. It interacts with a wedge element 32 of complementary structure on the distal receiving sleeve 2. The wedge elements 31, 32 are arranged such that they come to lie against each other with their beveled surface. The wedge element 32 has two receiving bores 34 which are located one behind the other in the axial direction of the receiving sleeve 2 and which, in the assembled state, are aligned with two receiving bores 33 arranged correspondingly one behind the other in the axial direction on the receiving sleeve 1. An inner thread is formed in the receiving bores 33. In the assembled state, a locking screw 39 is screwed into the aligned bores 34, 33 and engages in the inner thread of the receiving opening 33 and is thus tightened. This has the effect that the two wedge elements 31, 32 of the coupling piece are drawn tightly against each other and thus form a force-fit and also form-fit connection. This connection can take up extraordinarily high forces and, by virtue of the wedge action, is also free of play.

As an example of the dimensions of the illustrative embodiment, a length of ca. 90 mm is chosen for the receiving sleeves 1, 2, and a length of ca. 25 mm is chosen for the coupling piece. The width of the interior 10 is about 18 mm in the area of the end face and is about 15 mm in the deeper, narrowed area. The overall diameter of the receiving sleeve is about 30 mm. The wedge elements 31, 32 preferably have a width and, in the assembled state, also a thickness of about mm. In the illustrative embodiment shown, an advantageous variant is depicted, namely one in which the width of the receiving space in the proximal receiving sleeve 2, i.e. in the interior 20, is slightly greater by comparison with that of the interior 10 of the distal receiving sleeve 1. This has the effect that the generally larger shaft 96 of a hip prosthesis 94 can therefore be pushed only into the interior of the proximal receiving sleeve 2 and not the other way. This results, on the one hand, in better support and, on the other hand, in less risk of mix-up.

Figure 4:
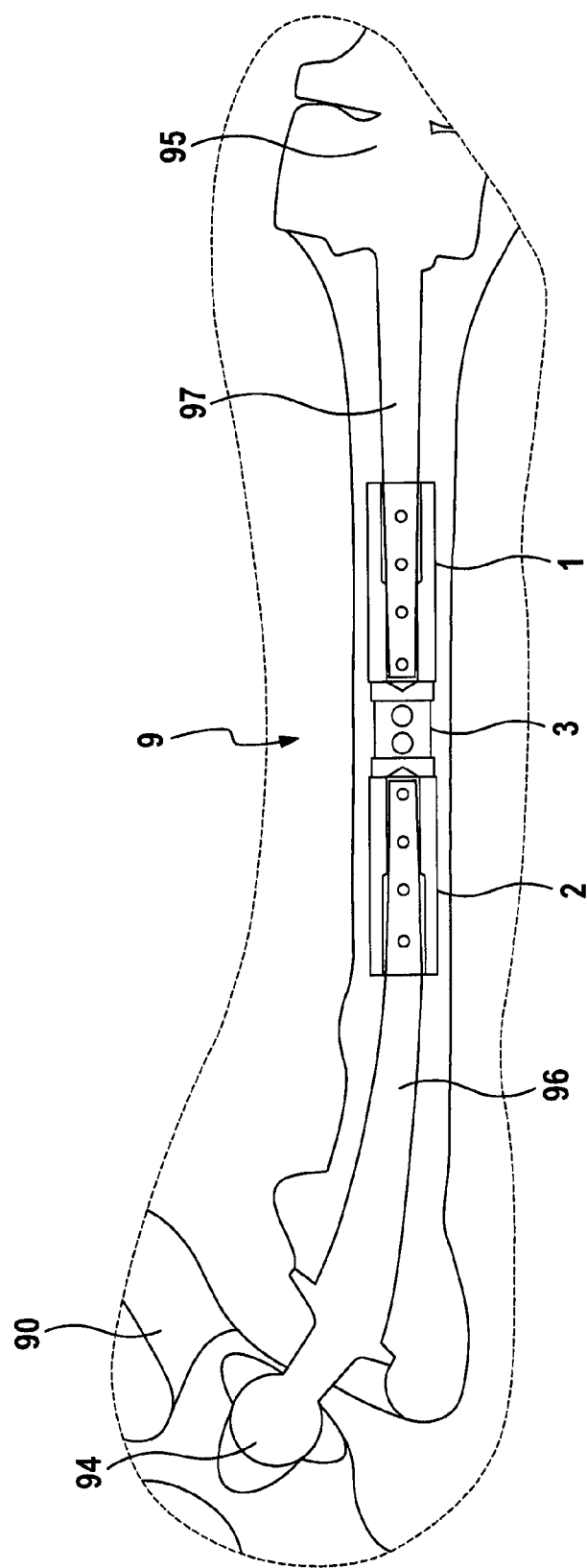
FIG. 4 shows the reinforcing implant in the implanted state on a femur, as seen on an X-ray image.

The use of the illustrative embodiment of the reinforcing implant according to the invention is explained with reference to FIGS. 4 and 5. The starting point is the situation shown in FIG. 5, where there is a fracture 9 of a femur 9. The femur 9 has been fitted with an artificial hip joint 94 which is implanted by an anchoring shaft 96 in a proximal part 92 of the femur 9. At the opposite, distal end of the femur, a knee-joint prosthesis 95 has been implanted, which is secured by its anchoring shaft 97 in a distal area 91 of the femur. The X-ray image as per FIG. 5 clearly shows the two anchoring shafts 96, 97 and how far they protrude into the medullary canal of the femur 9 until they almost touch each other. It will also be seen here that the proximal distal areas 92, 91 are each reinforced by the respective anchoring shaft 96, 97 pushed into this area, but the area lying in between is not reinforced. This gives rise to the problem mentioned at the outset and concerning the uneven loading of the femur 9. In the prior art, it has been attempted to secure a bone plate 98 on the outside of the femur in order thereby to reinforce the intermediate area. As is known, this measure is often inadequate in practice, since the bone plate 98 breaks and its fastening screws are torn out.

The necessary fastening stability can be achieved with the reinforcing implant according to the invention. The reinforcing implant is pushed with one part, preferably the distal part comprising the distal receiving sleeve 1, onto the free end of the anchoring shaft 97 of the knee-joint prosthesis 95. The wedge element 31 points toward the center of the femur 9, i.e. in the proximal direction in this case. Then, in an opposite move, the proximal receiving sleeve 2 is pushed onto the anchoring shaft 96 of the hip-joint prosthesis 94, its wedge element 32 likewise pointing toward the center of the femur, in this case in the distal direction. Fastening screws 29 are screwed into the respective fastening holes 15, 16 and 25, 26 both components, until the anchoring shafts 96, 97 are each fixed. The fastening by means of the screws in this case permits a variability with respect to the axis, i.e. the anchoring shafts 96, 97 can have axis deviations but are nevertheless held securely in the elements of the reinforcing implant. Both elements are pushed from their respective end into the medullary canal of the femur 9 until the wedge elements 31, 32 come into contact with each other (as shown in FIG. 1). In this situation, the coupling element 3 is joined together, such that the locking screws 39 can be screwed into the openings 33, 34 and tightened. The implant is thereby fixed. A continuous connection is obtained which, by virtue of this coupling, is stable. Fractures, as shown in FIG. 5, are thereby reliably avoided.

The invention claimed is:

1. An reinforcing implant for coupling anchoring shafts of two different prostheses which are arranged opposite each other on an elongated bone, the anchoring shafts being configured to anchor the respective prosthesis directly to the elongate bone, where the implant has a generally elongate shaft-like shape and comprises:
    a receiving sleeve at both ends for receiving an end of a respective anchoring shaft and,
    lying between the receiving sleeves, a disconnectable coupling piece for rigidly connecting the receiving sleeves after the anchoring shafts are received in the receiving sleeves and implanted in the elongate bone, and wherein the coupling piece comprises a connector, the connector comprising complementary beveled surfaces for coupling the receiving sleeves together,
    wherein, when the reinforcing implant is implanted in the elongate bone, the coupling piece is located between the ends of the anchoring shafts that are received in the receiving sleeves so that the reinforcing implant bridges an intermediate area between the anchoring shafts,
    wherein multiple fastening holes are arranged in rows on each of the receiving sleeves, said fastening holes being configured to receive fastening screws, and
    wherein the receiving sleeves with the fastening holes are configured such that a poly-axial seat for the anchoring shafts is formed, the poly-axial seat having an angle deviation to an axis of the receiving sleeves.

2. The reinforcing implant of claim 1, wherein the receiving sleeves comprise universal sockets for coupling anchoring shafts of different dimensions.

3. The reinforcing implant of claim 2, comprising a receiving bore in the receiving sleeves, the width of the receiving bore being stepped.

4. The reinforcing implant of claim 1, wherein the fastening holes on at least one of the receiving sleeves are axially offset about a circumference of the at least one of the receiving sleeves.

5. The reinforcing implant of claim 1, wherein the fastening screws have conical tips.

6. The reinforcing implant of claim 5, wherein the conical tips are made of hard metal.

7. The reinforcing implant of claim 1, wherein the fastening holes comprise securing devices which prevent accidental loosening.

8. The reinforcing implant of claim 1, wherein the receiving sleeves have a length that is at least three times the width of the anchoring shafts.

9. The reinforcing implant of claim 1, wherein the coupling piece has a length that is less than the width of the receiving sleeves.

10. The reinforcing implant of claim 9, wherein the beveled surfaces are arranged in opposite directions.

11. The reinforcing implant of claim 9, comprising locking screws for the connector.

12. The reinforcing implant of claim 11, wherein the locking screws are oriented such that the locking screws are in line with at least one row of the fastening holes on the receiving sleeves.

13. The reinforcing implant of claim 1, wherein the elongate bone is a femur.

14. The reinforcing implant of claim 1, wherein the angle deviation is an angle of up to 10° to the axis of the receiving sleeves.

15. The reinforcing implant of claim 1, wherein the coupling piece comprises a first portion that extends from a first one of the receiving sleeves and a second portion that extends from a second one of the receiving sleeves, and the first and second portions are disconnectable from one another.

16. The reinforcing implant of claim 1, wherein the receiving sleeves each comprise a cavity for receiving the end of a respective anchoring shaft and the cavity extends only partially through the receiving sleeve.

* * * * *